(12) United States Patent
Doyle et al.

(10) Patent No.: US 11,153,463 B2
(45) Date of Patent: Oct. 19, 2021

(54) REGION OF INTEREST TABLE

(71) Applicant: Carl Zeiss Meditec, Inc., Dublin, CA (US)

(72) Inventors: Michael Doyle, Oakland, CA (US); Keith E. O'Hara, Pleasanton, CA (US); Csaba Farkas, Pleasanton, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 107 days.

(21) Appl. No.: 16/145,022

(22) Filed: Sep. 27, 2018

(65) Prior Publication Data

US 2020/0106929 A1 Apr. 2, 2020

(51) Int. Cl.
*A61B 3/14* (2006.01)
*A61B 3/12* (2006.01)
*H04N 3/14* (2006.01)

(52) U.S. Cl.
CPC ............. *H04N 3/1562* (2013.01); *A61B 3/12* (2013.01); *A61B 3/14* (2013.01)

(58) Field of Classification Search
CPC ........... G06K 7/10881; G06K 7/10722; G06K 7/1098; G06K 7/10732; G06K 7/0004; G06K 7/089; G06K 7/10574; G06K 7/10851; G06K 7/14; G06K 7/10584; G06K 7/10861; G06K 7/109; G06K 7/10831; G06K 7/1439; G06K 7/10801; G06K 7/1465; G06K 2207/1017; G06K 7/10821; G06K 7/10841; G06K 7/1417; G06K 7/10811; G06K 9/22

USPC .......... 351/200, 205–206, 209–211, 221–223
See application file for complete search history.

(56) References Cited

U.S. PATENT DOCUMENTS

| | | |
|---|---|---|
| 3,915,564 A | 10/1975 | Urban |
| 5,083,119 A | 1/1992 | Trevett et al. |
| 7,768,652 B2 | 8/2010 | Everett |
| 8,025,403 B2 | 9/2011 | Maloca et al. |
| 8,488,895 B2 | 7/2013 | Muller et al. |
| 8,896,657 B2 | 11/2014 | Wang et al. |
| 8,922,768 B2 | 12/2014 | Brown et al. |
| 9,549,672 B2 | 1/2017 | Westphal et al. |
| 2010/0128221 A1 | 5/2010 | Muller et al. |
| 2016/0277684 A1* | 9/2016 | Park .................... G02B 27/646 |
| 2017/0049323 A1 | 2/2017 | Bublitz et al. |

(Continued)

OTHER PUBLICATIONS

Fossum et al., "A Review of the Pinned Photodiode for CCD and CMOS Image Sensors", IEEE Journal of the Electron Devices Society, vol. 2, No. 3, May 2014, pp. 33-43.

(Continued)

*Primary Examiner* — Brandi N Thomas
(74) *Attorney, Agent, or Firm* — Morrison & Foerster LLP

(57) ABSTRACT

A camera capable of quickly updating a region of interest (ROI) in its sensor array is provided. The camera is configured to image individual scan lines of a scan imager created as a scan beam is scanned across a subject. A different ROI is defined for each scan line to be imaged. To achieve this, a table of ROI-defining entries is loaded into the camera prior to imaging the scan lines. The ROI-defining entries are used to update the sensor's ROI during the camera's Frame-Overhead-Time. In this manner, the ROI is changed in between the imaging of consecutive scans lines.

21 Claims, 10 Drawing Sheets

(56) References Cited

U.S. PATENT DOCUMENTS

2017/0347872 A1 12/2017 Ozaki et al.
2018/0014727 A1 1/2018 Bublitz et al.

OTHER PUBLICATIONS

Liang et al., "Analysis and Compensation of Rolling Shutter Effect", IEEE Transactions on Image Processing, vol. 17, No. 8, 2008, pp. 1323-1330.

* cited by examiner

| ROI ID | Y-Offset | Number of Rows | X-Offset | Row Length | Exposure Time |
|---|---|---|---|---|---|
| ROI_1 | Y-Offset_1 | #Rows_1 | X-Offset_1 | X-Length_1 | ExP_Time_1 |
| ROI_2 | Y-Offset_2 | #Rows_2 | X-Offset_2 | X-Length_2 | ExP_Time_2 |
| •••• | •••• | •••• | •••• | •••• | •••• |
| ROI_i | Y-Offset_1 | #Rows_1 | X-Offset_1 | X-Length_1 | ExP_Time_1 |
| ↑221 | ↑222 | ↑223 | ↑224 | ↑225 | ↑226 |

ROI_Pointer_1 →

Optional ROI_Pointer_2 →

REGION OF INTEREST TABLE

FIELD OF INVENTION

The present invention is generally directed to the field of scan imagers. More specifically, it is directed to a line scan fundus imager having a full-frame camera with an improved mechanism for capturing multiple scan lines of a given, or varied, width within the same scanning sequence.

BACKGROUND

Various different types of image-capture devices for imaging a sample under test are known. Of particular interest are imaging systems capable of taking close-up images of a specimen with sufficient detail, e.g., sufficient focus, lighting, magnification, and signal-to-noise ratio (SNR). An example of such an imaging system is a fundus imager, which is typically used to image the fundus of an eye. The fundus is the interior surface of the eye opposite the eye lens (or crystalline lens) and may include the retina, optic disc, macula, fovea, and posterior pole. Two categories of imaging systems used to image the fundus are flood illumination imaging systems (or flood illumination imagers) and scan illumination imaging systems (or scan imagers).

Flood illumination imagers flood with light an entire field-of-view (FOV) of interest of a specimen at the same time, such as by use of a flash lamp, and capture a full-frame image of the specimen (e.g., the fundus) with a full-frame camera (e.g., a camera having a two-dimensional (2D) photo sensor array of sufficient size to capture the desired FOV, as a whole). For example, a flood illumination fundus imager would flood the fundus of an eye with light, and capture a full-frame image of the fundus in a single image capture sequence of the camera.

FIG. 1 is a conceptual illustration of a flood illumination fundus imager 10. A flash-tube 15 is shown as an illumination source, whose illumination light follows an optical path along illumination axis 17, which may include various system lenses 19, and is folded by mirror 23 onto optical axis 25, which includes system lens 11, to be conveyed to the sample, or specimen, to be imaged (e.g., retina 33 of eye 13 in the present example). System lens 11 is the imager lens closest to the eye 13, and may herein be termed an ocular lens or ophthalmic lens. Optical axis 25 traverses the optical components of the eye 13 (including the cornea 27, iris 28, pupil 29, and crystalline lens 31) to reach the retina 33. Thus, illumination light traveling along optical axis 25 may enter the eye 13 through its cornea 27, pass through its pupil 29, and traverse crystalline lens 31 to flood the retina 33 with light at the back of the eye (e.g., the fundus area), and be scattered by the retina 33 (and other parts of the fundus). Scattered light returning from the fundus may exit through the crystalline lens 31, pupil 29, and cornea 27, and travel along optical axis 25 to a viewing axis 35. Viewing axis 35 may include multiple system lenses 21, and directs the scattered light returning from the fundus to a full-frame camera 37 (e.g., a detector), which includes a 2D photosensitive area. For example, the 2D photosensitive area may be embodied by a 2D sensor array of photosensitive elements (e.g., photocells, photodiodes, phototransistors, etc.). The entire field-of-view (FOV) 38 of the fundus is captured as a whole by the 2D sensor array to produce a full-frame image 39 of the fundus of the eye 13. Since viewing axis 35 and illumination axis 17 are coincident along optical axis 25, mirror 23 typically has a centrally located aperture 43 used to permit scattered light returning from eye 13 to pass through mirror 23 onto viewing axis 35 to be captured by camera 37. Mirror 23 may be flat and annular (e.g., ring-shaped) with round aperture 43 at its center. Mirror 23 may further be imaged to the pupil 29 if it is used for pupil splitting.

Pupil splitting permits illumination light (light entering the eye 13) and returning light (scattered light exiting the eye) to follow different paths into and out of the eye 13, at optimally chosen regions of the pupil. These regions may be chosen, for example, to avoid pupil clipping (e.g., avoid part of the light from being blocked/clipped by the iris 28 whose center defines the pupil 29), light scattering due to cataracts (e.g., clouded regions of the crystalline lens 31), and specular reflections (e.g., reflexes) from the cornea 27, such as due to the illumination light. To ease implementation of pupil splitting, mirror 23, which reflects illumination light towards the eye 13 and whose aperture 43 permits passage of returning light to the camera 37, may be imaged at (e.g., be conjugate to), or near, the pupil 29. For example, when mirror 23 folds (e.g., reflects) illumination light from illumination axis 17 onto optical axis 25 towards eye 13, an annular-shape illumination region may be created at the eye 13 (e.g., near the pupil 29) due to the mirror's rounded aperture 43. That is, round aperture 43 of mirror 23 may create a round, non-illuminated region near the cornea 27 at the center of the annular-shaped illumination region. Scattered light may exit the eye 13 through this non-illuminated region and thereby avoid illumination light entering the eye 13. Additionally, specular artifacts from optical surfaces of the flood illumination imager itself may be reduced by using so-called dark spots, which are stationary in illumination paths and carefully positioned to prevent certain surface areas of system optics from being illuminated. Flood illumination imaging systems may image a fundus quickly, and have a high signal level and dynamic range, but may suffer from issues of low contrast. The need to eliminate reflexes may also place constraints on the system which may limit its FOV. An example of a flood illumination imaging system is found in U.S. Pat. No. 3,915,564, assigned to the same assignee as the present invention, and herein incorporated in its entirety by reference.

By contrast, a confocal point scanning fundus imager uses a coherent point beam of light that is scanned both vertically and horizontally across a desired FOV of a sample (e.g., the fundus), and image-captures one point-illuminated portion, or spot, of the fundus at a time. That is, the desired, full FOV is not captured as a whole in a single image capture sequence of a camera. Rather, as the point beam is scanned across the sample, illuminating a different point of the sample at each scanning step, the returning (e.g., refracted or reflected) light passes through a pinhole to reach a single, predefined location on a photodetector (or collector) that captures a point-portion (e.g., a pixel of image data) of the sample at a time (e.g., at each scanning step). The pinhole helps to eliminate out-of-focus light signal by allowing only the center of the returning light beam to reach the photodetector (e.g., the outer, diffused portion of the returning light beam is blocked). The returning light reaches the same point-location on the photodetector (e.g., of a charged coupled device, CCD, camera) irrespective of scan position of the scanning point beam on the sample, and many individual point-portions (e.g., pixels of image data) need to be captured in sequential image capture sequences of a camera to create a full frame image. The many, captured point-portions resulting from one full scan of the desired FOV of the sample are montaged together to create a composite image, which may constitute a full-frame image.

FIG. 2 illustrates a simplified, exemplary scanning pattern of a confocal point scanning fundus imager. It is to be understood that other scanning patterns, such as circular or spiral patterns, are possible. In the present, illustrative example, each point (e.g., point-illuminated portion) Sp_1 to Sp_n is captured separately and individually in a scanning pattern. Since only one point in the sample is illuminated and captured at a time, imaging typically requires scanning over a regular raster (e.g., a rectangular pattern of parallel scanning rows of spots) on the sample, e.g., the fundus. For example, a laser point beam may be scanned across the sample in an X-Y plane (perpendicular to a primary axial direction (e.g., Z-axis) of the point beam) by using one or more scanning components (e.g., servo controlled rotating, or oscillating, mirrors, or galvanometers). For example, a separate row (e.g., R1 to Rm) of points may be captured in corresponding separate horizontal scans, H-scan, one after another, and the scanning point beam may be scanned vertically in one-row-offset incremental steps (e.g., one vertical step after each horizontal scan) to define a vertical scan, V-scan. Typically, slower scans may provide a better signal-to-noise ratio, resulting in better contrast and higher resolution.

Due to the point confocal arrangement of illumination and detection, the confocal point scanning fundus imager may advantageously suppress stray-light and out-of-focus light, and thereby produce high contrast images without the need for pupil splitting. Thus, a benefit of the confocal point scanning fundus imager over the flood illumination fundus imager is an increased level of confocality, which provides greater discrimination against undesirable light scattered from surfaces other than the target point to be imaged. However, since the confocal point scanning fundus imager operates with point illumination, it may require high intensities which raise safety issues when imaging a retina. Similarly, since much of the returning light from the sample is blocked by the pinhole leading to the photodetector, its increased resolution is generally at the cost of decreased signal intensity so that its exposure time may need to be elongated. Additionally, the confocal point scanning fundus imager generally requires multiple scanning components (e.g., multiple galvanometers, or galvos) to achieve horizontal and vertical scans, which can be expensive and complicated, and can slow their image production since many points need to be collected to construct a full-frame composite image. This also may raise issues of eye movement during the collection of an image, which may lead to image distortions.

A line scanning imager (e.g., a laser-line scanning imager or broad-line scanning imager) may be thought of as a combination of a confocal point scanning imager and a flood illumination imager. A line scanning imager illuminates a linear strip of a sample (e.g., the retina) at a time. The linear strip may simultaneously illuminate, for example, a length-span extending from a left-most boundary of a desired FOV to the right-most boundary of the FOV, or equivalently, extending from a top-most boundary of the desired FOV to the bottom-most boundary of the FOV. The linear strip is scanned across the sample (e.g. either vertically or horizontally), and thereby illuminates the entire FOV in one sweep, in a piecemeal fashion. The camera of the line scanning imager captures one strip-portion of the sample at a time, which may then be combined/montaged to create a composite full-frame image.

As can be seen from the above discussion, different fundus imagers generally have different photodetector requirements. Consequently, specialized photodetector (e.g., photo sensor, photosensitive element array, camera) configurations and operations may be needed, for different types of fundus imagers, which can complicate the designs and construction of a fundus imager.

It is an object of the present invention to provide a camera architecture and operating method that may be used with different types of fundus imagers.

It is a further object of the present invention to provide a camera that is configurable to support on-the-fly changes in accordance with changes in individual scan lines within a scanning sequence.

SUMMARY OF INVENTION

The above objects are met in a camera architecture and operation method for quickly updating a region of interest (ROI) in its sensor array. The camera may be configured to image individual scan lines of a scan imager created as a scan beam is scanned across a subject. A different ROI is defined and implemented for each scan line to be imaged. To achieve this, a table of ROI-defining entries is loaded into the camera prior to imaging the scan lines. The ROI-defining entries are used to update the sensor's ROI during the camera's Frame-Overhead-Time. In this manner, the sensor's ROI may be changed in between the imaging of consecutive scan lines.

The present invention provides a method for controlling a camera of a scan imager (e.g., fundus line scan imager). The scan imager uses a scanning mechanism to produce a scan beam that may define different scan lines of a scanning sequence across a subject, such as an eye fundus. The camera is used to image individual scan lines of the scanning sequence, including: defining a region-of-interest (ROI) within the camera's sensor array to image a currently defined scan line, and updating the ROI before imaging a subsequent (e.g., the next consecutive) scan line in the scanning sequence. A composite image from the fundus may be constructed from the individually imaged scan lines. In order to quickly update the sensor's ROI, the present camera configuration removes the need for external instructions from a user for ROI updates, as is the norm in the prior art. Rather, the present camera architecture maintains an ROI-definition record (e.g., register) that defines an ROI in the sensor, and stores an ROI Table of entries. Each entry in the ROI Table defines a different ROI for a corresponding scan line. Optionally, the entries in the ROI Table may have a one-to-one correspondence with the scan lines of the scanning sequence. The ROI table may be loaded into the camera prior to starting the imaging of the scanning sequence. In operation, the ROI-definition record is updated in between the imaging of consecutive scan lines in accordance with the ROI Table.

The present invention also provides a method for controlling a camera for defining a region-of-interest (ROI) in a sensor array in accordance with an ROI-definition record. The camera executes an image capture sequence, including: actuating image capture of the ROI (e.g., initiation pixel exposure within the region of interest to integrate photonic energy at each photosensitive element, or pixel) in response to a capture-start signal; terminating the image capture of the ROI (e.g., ending pixel exposure) in response to a capture-stop signal; and reading out the captured image data of the ROI; and updating the ROI-definition record during the execution of the image capture sequence. As it would be understood, the image capture sequence may further include a signal conditioning phase following the terminating of the image capture of the ROI (e.g., following the ending of pixel exposure). This signal conditioning phase may include amplifying pixel signals and converting them to digital form prior to the step of reading out the captured (e.g., conditioned) image data of the ROI. This may provide for a delay phase (e.g., wait period) between the ending of the image capture phase and start of the reading out phase. Preferably, the ROI-definition record is updated during this wait period.

Since the scan line may be scanned (vertically or horizontally) across a subject, updating the ROI may include updating an offset position within the sensor array in at least one of an X-axis direction or Y-axis direction.

Optionally, the ROI-defining record may be updated in accordance with an ROI Table of entries, where each entry defines a different ROI. If the camera supports multiple different imaging modalities, then each image modality may have a corresponding, different ROI Table.

The present invention also provides a camera including: an image sensor array; a region-of-interest (ROI) definition record that defines a region of interest within the image sensor array; and control circuitry to implement a specialized imaging sequence. This sequence may include: (i) an image capture sequence, including: initiating exposure of the sensor array to image the defined region of interest in response to a capture-start signal; terminating the exposure of the sensor array in response to a capture-stop signal; and reading out image data of the defined region of interest; and (ii) a step of updating the ROI-definition record during the execution of the image capture sequence. The camera may be configured to image individual, consecutive scan lines from a scan imager during a scanning sequence of the scan imager. In this case, the ROI-definition record may be updated in between the imaging of consecutive scan lines within the scanning sequence.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Any embodiment feature mentioned in one claim category, e.g. method, can be claimed in another claim category, e.g. system, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts:

FIG. 10 illustrates an exemplary ROI Table.

DESCRIPTION OF THE PREFERRED EMBODIMENTS

Figure 1:
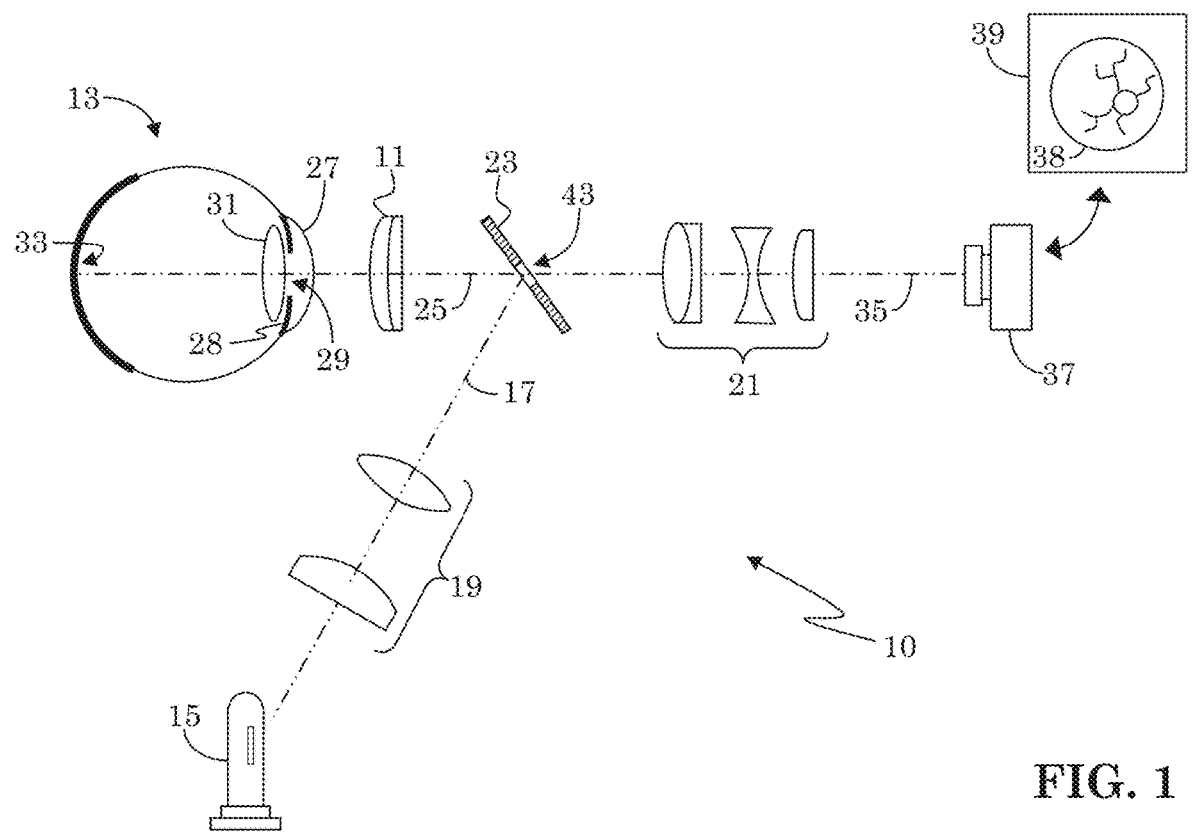
FIG. 1 is a conceptual illustration of a flood illumination fundus imager.
Figure 2:
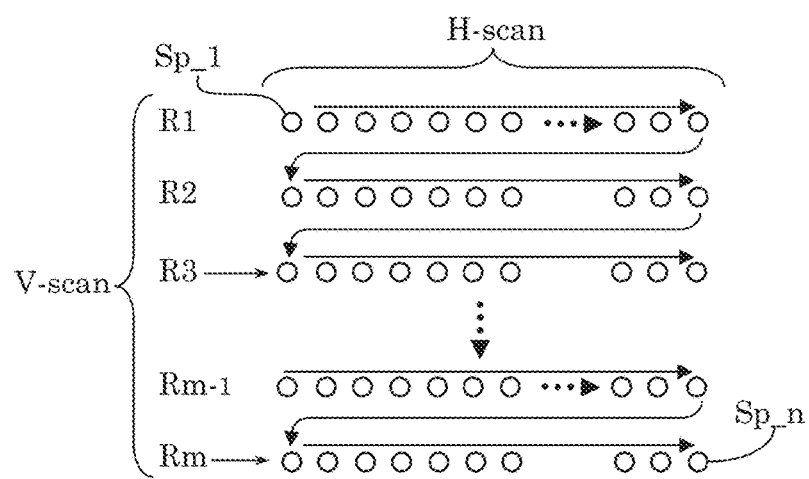
FIG. 2 illustrates a simplified, exemplary scanning pattern for a confocal point scanning fundus imager.

The following provides a new camera architecture and operation method for more flexible manipulation of regions of interest within the camera's sensor array. The camera is well suited for use in fundus scan imagers of different types and of different scanning configurations. A scan imager provides a scan beam that is scanned across a subject, and the scan beam is imaged at different scan positions as it is scanned across the subject. The present invention provides a method and architecture for updating a region of interest of the sensor array in between consecutive imaging of scan beams at consecutive scan positions. Since the present invention may be implemented in scan imagers of different types and different scanning configurations, an overview of some of these types and configurations, along with some limitations of current camera technologies, is first presented.

Two types of scan imagers are the confocal point scanning imager and the line scanning imager. The confocal scan imager generally uses a laser point beam to scan a sample one point at a time. The line scanning imager may use a narrow line beam (e.g., the laser-line scanning imager) or a broad line beam (e.g., the broad-line scanning imager) to scan a sample one line at a time. In the field of fundus imagers, the line scanning imager may be termed a line scanning ophthalmoscope, and includes both the line-scanning laser imager/ophthalmoscope, LSLO, which is an example of a laser-line scanning imager and typically uses a laser to produce a very narrow traversing line across a sample as it scans, and the broad-line scanning (fundus) imager/ophthalmoscope, BLFI, which is an example of a broad-line scanning imager and may use a non-coherent light source to produce a traversing broad line (or slit) of predefined width across a sample as it scans. U.S. Pat. No. 7,768,652, which is herein incorporated in its entirety by reference, provides a description of an LSLO. Examples of broad-line scanning imagers may be found in U.S. Pub. No. 2017/0049323 and U.S. Pub. No. 2018/0014727, both assigned to same assignee as the present invention and both herein incorporated in their entirety by reference. Hereinafter, the term line scanning imager may be understood to refer to both, or either, of a laser-line (or very narrow-line) scanning imager (e.g., LSLO) and a broad-line scanning imager (e.g., BLFI).

Scan imagers may include a digital camera (e.g., photodetector or photosensor array) to capture scattered light returning from each scanned position of a sample. The individually imaged scan positions may then be collected in series across the area of the detector or montaged together after collection to create a composite image of the sample, which may define a full-frame (e.g., full field-of-view, FOV) image. For ease of discussion, some embodiments of the present invention describe the use of scan imagers to image the fundus of an eye, which is the interior surface of the eye opposite the eye lens (e.g., crystalline lens) and may include the retina, optic disc, macula, fovea, and posterior pole. That is, the presently discussed scan imagers may be presented within the context of fundus scan imagers, but it is to be understood that the present invention may likewise be used in scan imagers optimized for other uses, e.g., to image samples other than an eye. Similarly, particular digital camera embodiments are herein described within the context of fundus imaging, but it is to be understood that the present digital cameras embodiments may likewise be implemented in other imaging applications.

The above scan imagers may use different radiation sources (e.g., a laser for the coherent point scanning imager and the laser-line scanning imager, and a non-coherent light source such as a lamp or light emitting diode(s), LEDs, for the broad-line scanning imager), but each will generally produce a radiation stream or beam that is conveyed (along a radiation path) to a scanning mechanism/component (e.g., one or more mirror galvanometer (or galvo), micro electro mechanical system (MEMS) scanner, electro-optical deflector, rotating mirror, and/or rotating polygon scanner). The radiation beam (or illumination beam) output from the radiation source may be shaped by placing a slit (e.g., an aperture of specific configuration) in front of the radiation source. This slit aperture may be imaged to (e.g., be conjugate to) the fundus, or whichever surface is to be imaged. The scanning component receives the radiation beam from the radiation source and defines a scan beam that is scanned in a specified pattern. From the scanning component, the scan beam follows an optic train (that defines a scanning path) to exit the scan imager and scan across the sample (e.g., the eye fundus). This optic train typically includes a scan lens in front of the scanning component (along the scanning path) followed by one or more optics (e.g., lenses or lens structures) that direct the scan beam to the subject to be imaged.

Each type of scan imager has its advantages and disadvantages, and may be optimized for various uses. For example, the confocal point scanning imager inherently avoids defocused light, but since each imaged point (e.g., each captured scanned position) may correspond to one image pixel, it needs to be scanned laterally and vertically across a sample to construct a composite, full-frame image. This may lead to comparatively long image capture times. The line scanning imager generally achieves a measure of confocality in its width direction (perpendicular to the length dimension of the traversing scan line, or scanning line beam) and can be scanned across a sample more quickly than the point scanning imager. However, at least in the case of the broad-line scanning imager, a captured image may not achieve a desired brightness if the scanning line beam is too narrow. Nonetheless, the broad-line scanning imager can avoid the need for a laser source making it more cost effective than the other two scan imagers, and can further use a scanning line beam of different widths to optimize the amount of light applied to a sample being scanned. The different types of scan imagers place different requirements on the scan imager's photodetector (e.g., digital camera) that captures each discrete scan position. Furthermore, scan imagers may implement any of multiple different scanning configurations, each of which may place additional requirements (e.g., image capture time, size of photodetector area, location of photodetector area) on the scan imager's digital camera. Thus, selection and configuration of the digital camera used in a scan imager is a critical part of any scan imager implementation.

Nonetheless, line scanning imagers have facilitated the use of more traditional digital cameras as photodetectors, and their integration into multiple scanning configurations. For illustration purposes, some simplified scanning configurations are presented below, along with a description of different digital camera implementations. As will be evident, the slit fundus imager poses some challenges to the use of particular digital camera configurations with particular scanning configurations.

Before discussing some of these scanning configuration, it may be beneficial to provide a brief description of different types of digital cameras. Within the field of digital cameras, charged coupled device (CCD) cameras and complementary metal oxide semiconductor (CMOS) cameras are most common. Both generally use photodiodes as their photodetector element. More specifically, today most image sensors use a variant of the pinned photodiode as the preferred photosensitive element, as is explained in "A Review of the Pinned Photodiode for CCD and CMOS Image Sensor," *IEEE Journal of the Electron Devices Society*, Vol. 2, No. 3, May 2014, herein incorporated in its entirety by reference. However, other types of photosensitive elements are known in the art, and the specific type of photosensitive element is not critical to the present invention. A two-dimensional (2D) sensor array is comprised of multiple rows of photosensitive elements. The CCD camera was commercially developed prior to the CMOS camera, and enjoyed speed, imaging, and operational advantage over CMOS digital cameras for a while. For example, CCD cameras were the first to introduce a global shutter operation and capture an entire 2D sensor array (e.g., a full frame image) in a single shutter operation. In a global shutter operation, all the photosensitive elements in the 2D sensor array (e.g., the entire frame) are captured at the same instant/time, and the stored information from each photosensitive element may then be read out. In CCD cameras, their stored sensor array information is read out in a comparatively slow serial manner, which can increase the amount of time needed between image capture operations. Although CMOS cameras with global shutter capability have been developed, still today, most CMOS cameras use a rolling shutter to capture a full frame image. In a rolling shutter, one row of pixels (e.g., a single pixel row within a 2D sensor array of pixels rows) is captured at a time, in sequence, until all the pixels rows of the 2D sensor array are captured. This can lead to what may termed the rolling shutter effect, or distortion, if the subject being imaged moves between sequential captures of pixel rows. A description of the rolling shutter effect, and a method of compensating for it, is provided in "Analysis and Compensation of Rolling Shutter Effect," *IEEE Transactions on Image Processing*, Vol. 17, No. 8, August 2008, herein incorporated in its entire by reference. This distortion is particularly prevalent when imaging fast-moving objects. However due to the commercial success of CMOS technology, CMOS cameras have advanced more rapidly than CCD cameras, and have erased many of their previous disadvantages. Indeed, CMOS cameras today are less expensive than CCD cameras, and can be markedly faster than CCD cameras. As a result, CMOS cameras are now preferred for many commercial applications.

The desire for faster digital cameras has led to various imaging variants optimized for specific applications. For example, the line scan camera uses a one-dimensional array consisting of one row of photosensitive elements. Thus, it captures a single row of pixels during each image capture sequence (operation), but since its sensor array is smaller than a full-frame 2D array, it can achieve faster operational speeds (e.g., reduce the time between sequential image capture operations). For example, in a manufacturing line, a line scan camera may continuously image items as they are conveyed by the camera's scan line on a conveyer belt. This permits a quality assurance system to continuously visually inspect the passing items for defects. Images of the items on the conveyer belt may be reconstructed pixel row by pixel row, if necessary.

Advances in CMOS integration circuit design and manufacturing have also permitted the introduction of more sophisticated sensor array operations. For example, like in the case of the line scan camera, if one is interested in only one pixel row of data, a CMOS camera that has a 2D sensor array may be programmed to capture (e.g., latch and optionally amplify, and digitize) and read out (e.g., output) image information from only that pixel row and thus avoid the time that would have been required to capture and output all the imaging information from the entire 2D sensor array. This can reduce the amount of time needed between image capturing sequences without requiring a specialized line scan camera, and thereby be suitable for use in a scan imager. This type of operation may be implemented by defining a region-of-interest (ROI) within the camera's 2D sensor array (which defines a fraction of consecutive pixels rows within the 2D sensor array), and then executing an image capture sequence in which only image data from the designated ROI is captured and output. An ROI thus provides some light filtering benefits by behaving like an electronic shutter wherein image information from outside the ROI is effectively blocked. Traditionally in operation, an ROI is defined by inputting ROI information into the camera prior to initiating an image capture of a scanning sequence such that the same ROI is applied to all scan lines within the scanning sequence. Since individual scan lines within a scanning sequence move across a sample far more quickly than new ROI information could be input to the camera, it has heretofore not been possible to alter an ROI during a scanning sequence. That is, during an image capture sequence of a scanning operation by a scan imager, the ROI would remain fixed in location and size on the camera's 2D sensor array, and each sequential image capture operation of the camera would capture a current scan location of the scan imager at the same region-of-interest, ROI.

Although defining an ROI avoids reading image information from regions of the 2D sensor array that are not of interest, defining an ROI generally does not affect the image capture sequence of the camera. For example, a rolling shutter camera that has multiple ROIs defined will still capture one pixel row at time within each ROI across its 2D sensor array, but it may be possible to selectively skip pixel rows that are not within an ROI. Thus, having multiple ROIs does not alter the sequence in which an image is captured on the 2D sensor array. All ROIs are exposed and captured during the same image capture sequence, and one cannot selectively skip an ROI during an image capture sequence. Therefore, in a rolling shutter operation in which pixel rows are captured sequentially from top to bottom along the 2D sensor array, ROIs closer to the top will be captured before ROIs closer to the bottom of the 2D sensor array. Similarly in a global shutter application, all ROIs in the 2D sensor array will be captured at the same time. Since defining an ROI is part of an initialization step in preparation for an image capture sequence, defining an ROI has traditionally required an input sequence to the camera wherein a user inputs ROI instructions prior to initiating an image capture operation. It has been found that this input sequence to the camera is too slow for some scan imaging applications, even when using industry standard electronic communication techniques and/or protocols, such as the universal serial bus, USB®, or Camera Link®.

As will become clear from the following discussion, providing for improved manipulation of ROIs within a digital camera would facilitate the integration of digital cameras into scan imagers of different scanning configuration.

Various simplified scanning configurations suitable for scan imagers are provided below. For illustration purposes, these scanning configurations are presented within the context of a line scanning imager, but it is to be understood that the present scan configurations may also be applied to point scanning imagers.

Figure 3:
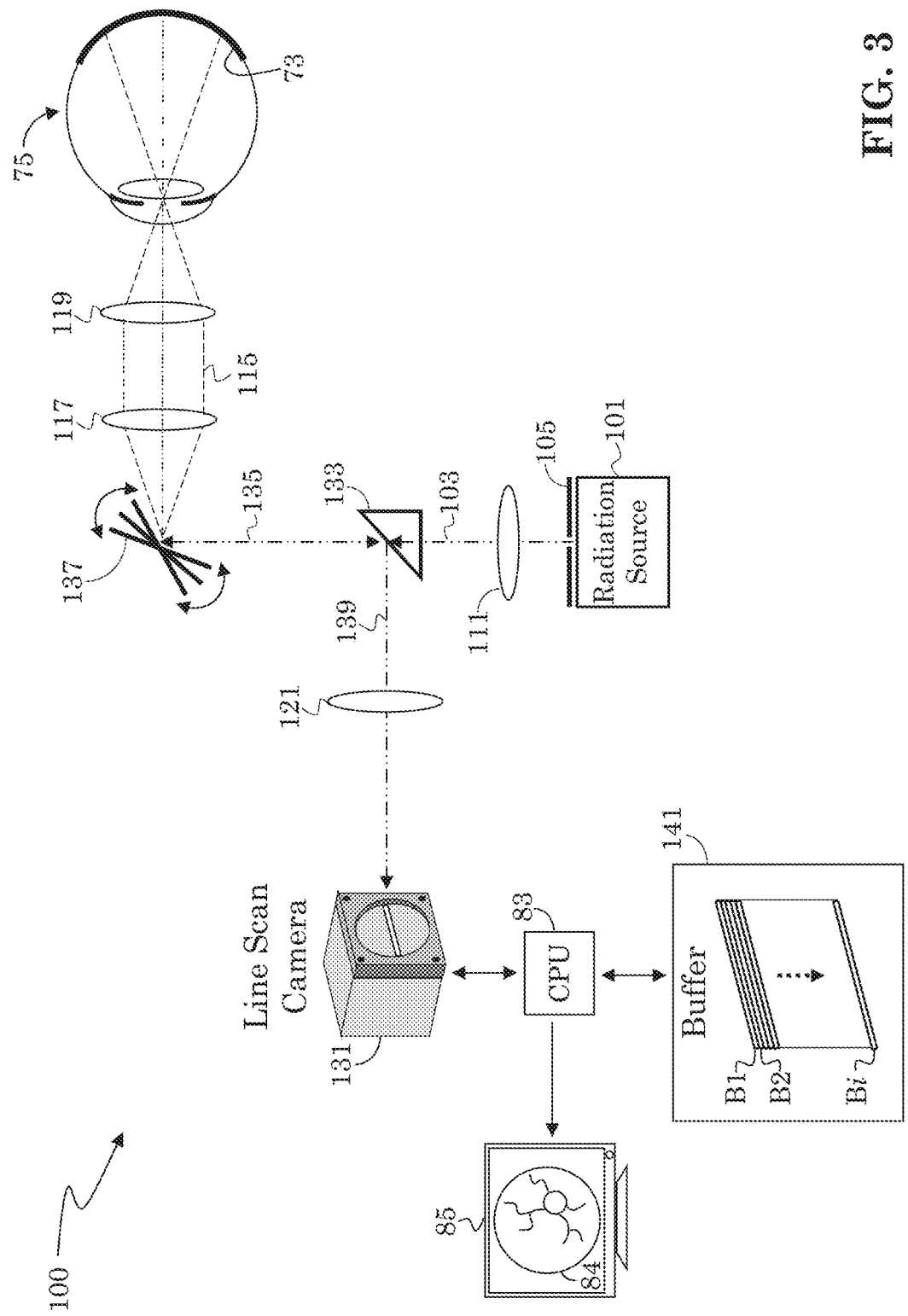
FIG. 3 illustrates an idealized scanning configuration of a so-called "scan-descan" line scanning imaging system, wherein a scanning line beam is scanned across a sample, but a line of returning light on a collection (optical) path from the eye is maintained at a stationary, predefined position on a detector and does not scan across the detector.

FIG. 3 illustrates an idealized scanning configuration of a so-called "scan-descan" line scanning imaging system 100, wherein a scanning line beam 115 is scanned across a sample (e.g., retina 73 of eye 75), but a line of returning (e.g., scattered) light on a collection (optical) path 139 from the eye 75 is maintained at a stationary, predefined position on a detector 131 and does not scan across the detector 131. A radiation source 101 (e.g. light source, such as a laser, lamp, or LED) produces an illumination line beam 103 (non-coherent light beam or laser beam). A radiation aperture 105, imaged to the sample surface that is to be imaged, may be placed in front of radiation source 101 to help shape the illumination line beam 103. In the case of a fundus scan imager, radiation aperture 105 may be imaged to the retina 73 of the eye 75.

Illumination line beam 103 may pass through one or more optics before reaching a scanning component 137. For example, the illumination line beam 103 may pass through a collimating lens 111 and a beam splitter (or beam divider) 133 to reach scanning component 137, which may take any of multiple different implementations, such as one or more mirror galvanometer, MEMS scanner, electro-optical deflector, and/or rotating polygon scanner. For example, if scanning component 137 is implemented as a mirror galvanometer, a mirror is made to rotate in order to scan the received illumination line beam 103 from beam splitter 133 in discrete steps (or in continuous, definable steps) to define a scanning line beam of radiation (e.g., scanning line beam 115) that defines illumination lines across the sample to be imaged (e.g., retina 73). Typically, a scan lens 117 and ophthalmic lens 119 is placed in the optical path between scanning component 137 and eye 75. Generally, the scan lens 117 receives a scan beam from scanning component 137 at any of multiple scan angles (incident angles), and produces scanning line beam 115 with a substantially flat surface focal plane (e.g., a collimated light path). Ophthalmic lens 119 then may focus the scanning line beam 115 onto the retina 73 of eye 75 to image the fundus. That is, scanning line beam 115 creates a traversing scan line (e.g., line of illumination) in this case traveling vertically across the retina 73.

Figure 4:
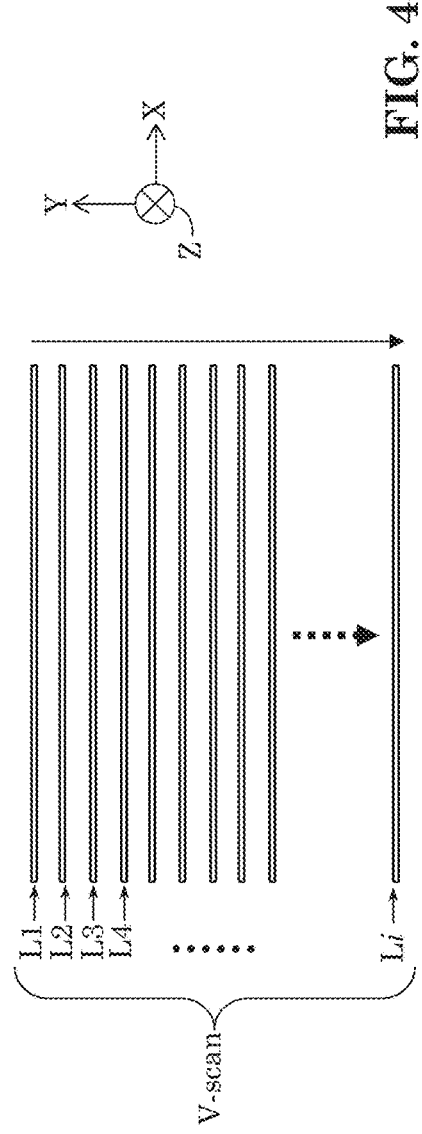
FIG. 4 illustrates a simplified, exemplary scanning pattern for a line scanning imager as they may be produced on the subject being scanned.

FIG. 4 illustrates a simplified, exemplary scanning pattern for a line scanning imager as they may be produced on the subject being scanned. In the present example, the scan lines are scanned (e.g., traversed) vertically to produce multiple scan lines L1 to Li in a vertical scan pattern, V-scan. As explained above, two types of line scanning imagers are the laser-line scanning imager and the broad-line scanning imager. For ease of discussion, scan lines L1 to Li may represent line scans as produced by a laser-line scanning imager or a broad-line scanning imager, with the understanding that scan lines produced by a laser-line scanning imager are typically much narrower than those produced by a broad-line scanning imager. Line scanning imagers, in general, may maintain some level of confocal suppression of out of focus light perpendicular (e.g., along the Y-axis in FIG. 4) to the scan line (L1 to Li), but lack confocal suppression along the line (e.g., along the X-axis in FIG. 4). The scan lines may also be used to enhance imaging. For example, the sharpness of the edge of an illumination strip may be used to find an optimized focus for the line scanning system for the case where the illumination has not moved significantly during an acquisition by the detector (typically when the scan beam is being scanned in steps and is relatively motionless during an acquisition). Locations on the retina that are not illuminated may be detected (e.g., image captured) to evaluate background levels, e.g., stray light levels, coming from out-of-focus regions of the eye, and this background level may then be subtracted from a captured line image. Line scanning imagers have also been combined with pupil splitting (see for example Muller et al. U.S. Pat. No. 8,488,895, which is herein incorporated in its entirety by reference). Advantageously, a line scanning imager can scan faster across the retina (or fundus) than a confocal point scanning imager, and is therefore less sensitive to motion artifacts, but at the expense of less out of focus suppression.

Returning to FIG. 3, at each scan step (e.g., as defined by individual scan lines L1 to Li in FIG. 4), light is reflected/scattered back (in a capture phase) to scanning component 137. For purposes of discussion, scanning component 137 may be assumed to be substantially stationary during this capture phase, and so reflects the returning light along the same optical path 135 as the illumination line beam from beam splitter 133, as illustrated by dual-headed arrows on optical path 135. The returning, stationary line of scattered light is directed by beam splitter 133 onto a collection path 139, which conveys it to the photodetector 131, herein illustratively implemented as a line-scan camera. As shown, scanning component 137 maintains the location of returned scattered light on collection path 139 substantially stationary irrespective of the vertical scan position of scan lines L1 to Li on retina 73, which is herein termed a "descan" operation. That is, scattered light exits eye 75, and returns through ophthalmic lens 119, scan lens 117, to reach scanning component 137. Because the scanning position of scanning component 137 when returning light reaches it is substantially similar to the position when a corresponding scanning line beam 115 was defined, scanning component 137 has the effect of "descanning" (or un-scanning) the returning light so that it is a steady line beam (non-scanning) by the time it is on optical path 135 and reaches beam splitter 133. At beam splitter 133, the returning light may be directed onto another focusing lens 121, which focuses the returning light beam onto photodetector 131. Each returning (scattered) light line is separately imaged (e.g., captured or detected) by the photodetector 131, as the scanning line beam 115 from the scanning component 137 is scanned across the retina 73.

Each captured returning light line (e.g., image strip) from each discrete scan step may be mapped to a buffer 141 to define a separate buffered line image B1 to Bi at positions corresponding to the scan positions of their corresponding scan line L1 to Li (see FIG. 4). The buffered line images may then be reconstructed (e.g., montaged) into a full frame image 84, such as by use of a CPU 83 (e.g., computing system or device) and rendered on a computer display 85. That is, the signal (e.g., line of light) that is detected by the photodetector 131 may be processed by CPU 83 to form full frame image 84, which may be displayed on video display 85, or stored in a memory associated with CPU 83 for further processing.

Because the returning light line on collection path 139 is not scanned, the location on the photodetector 131 that receives the returning line of light is fixed. This permits a choice of different digital camera types. In the case of the line-scanning laser ophthalmoscopes, LSLO, the radiation source 101 may be implemented as a laser, and thus produce a very narrow line beam, which produces narrow scan lines L1 to Li on the retina and a correspondingly narrow line of returning light that may define one line of pixels on a composite image. Since only one line of pixels needs to be captured, this permits the use of a line-scan camera as detector 131. The line scan camera generally has a one dimensional pixel array consisting of a single row of pixels (photosensitive elements) used to capture image data very quickly. Additionally, the line-scan camera may have a line-shaped aperture to improve the confocality of the light that reaches its sensor array.

In the case of a broad-line scanning imager, radiation source 101 may be implemented as a broader-beamed illumination source, such as LEDs or a lamp, and radiation aperture 105 may be used to shape the illumination line beam 103. For example, radiation aperture 105 may be widened to produce a broader illumination line beam 103, which may result in a much broader returning light line on collection path 139 whose width may span multiple rows (e.g., lines) of pixels on a composite image. This may preclude the use of a line-scan camera as photodetector 131. In this case, a more suitable choice may be a full-frame digital camera having a 2D sensor array.

Figure 5:
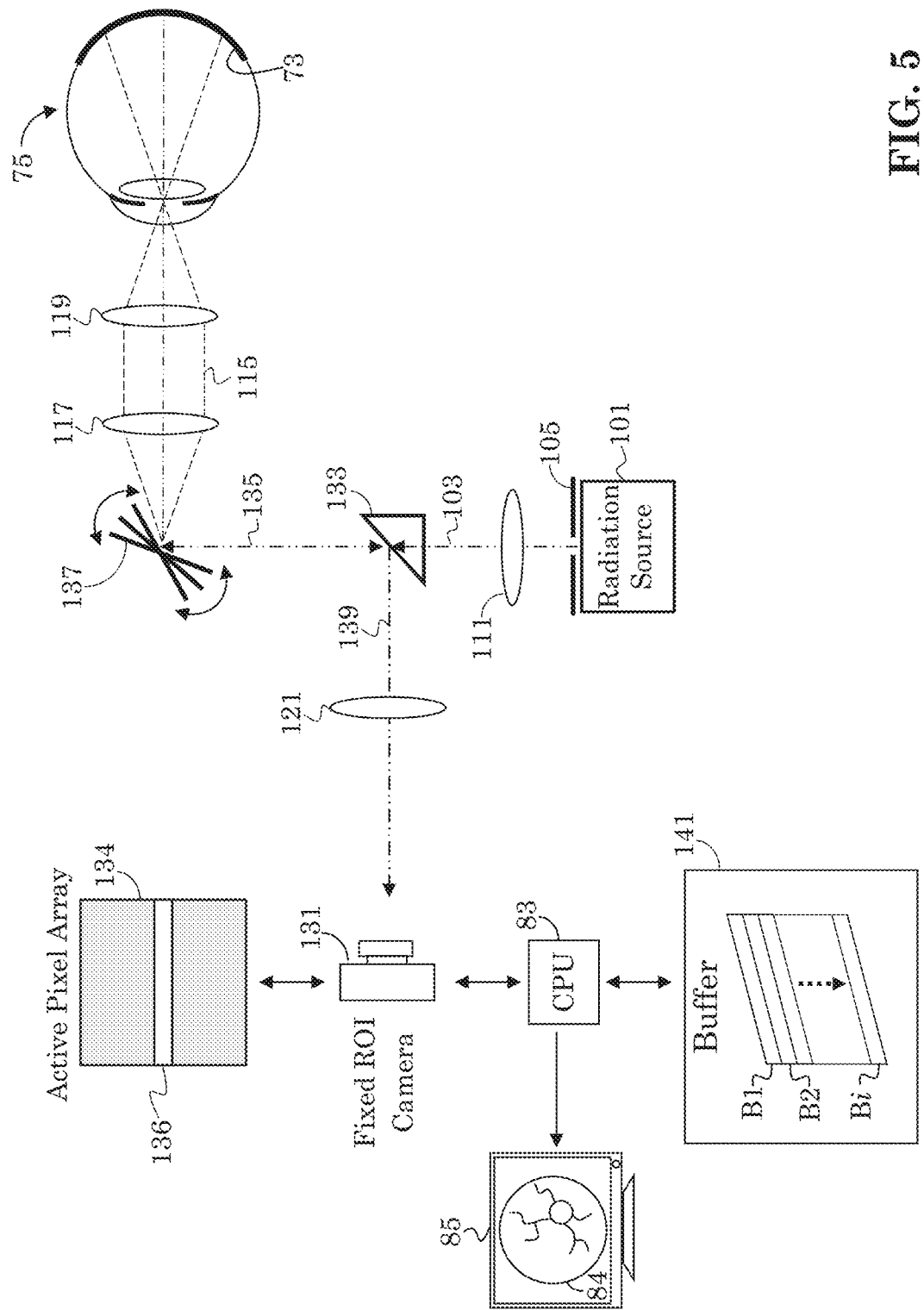
FIG. 5 illustrates the use of a full-frame digital camera in a line scanning imager having a scan-descan configuration, as in FIG. 3.

FIG. 5 illustrates the use of a full-frame digital camera in a line scanning imager having a scan-descan configuration, as in FIG. 3. All elements similar to those of FIG. 3 have similar reference characters and are described above. In the present example, the photodetector 131 is implemented as a full-frame digital camera, which includes a 2D sensor array (e.g., a 2D active pixel array) 134. As shown, the broad, returning light line on collection path 139 is detected within a predefined region 136 of the active pixel array 134. Thus, one small region 136 would capture image data during each image capture sequence of the digital camera 132. Since only a small region 136 of the pixel array is of interest during each image capture sequence, one may avoid reading pixel information from areas of the pixel array 134 outside this region 136, and thereby speed up the operation of the full-frame camera 132. That is, the digital camera may have the capability of defining one (or more) regions-of-interest, ROI, within its active pixel array 134, which defines multiple rows of pixels, and to output image information only from this ROI. In this case, the ROI may be selected to coincide with predefined region 136. That is, the ROI may be defined to span one or more consecutive rows of pixels, and thereby capture a broad returning line of a given width. It is noted, therefore, that a full-frame camera may also be used in a laser-line scanning imager in place of the line scan camera of FIG. 3 by defining a narrower ROI, e.g., an ROI defining one row of pixel elements.

Figure 6:
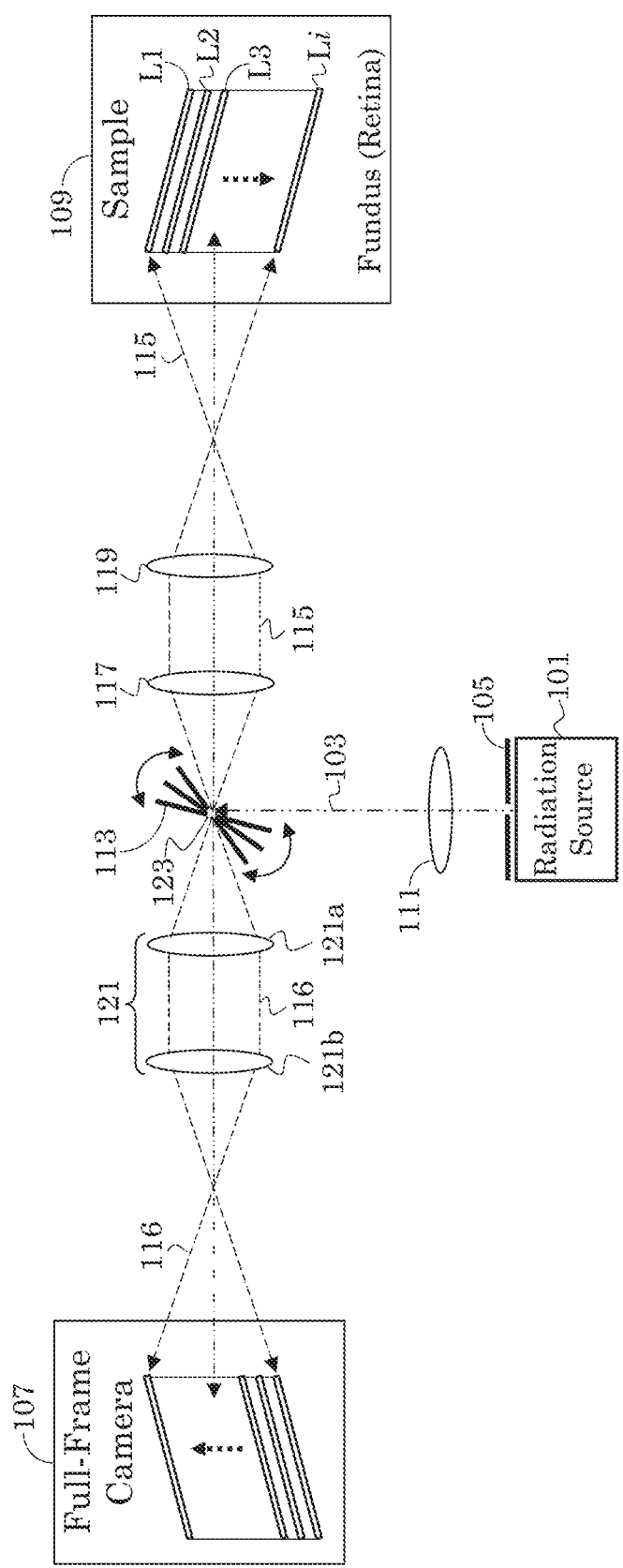
FIG. 6 illustrates a simplified, so-called, "scan-non-descan", scanning configuration wherein a scanning line beam illuminates scan lines traversing a sample in one dimension (e.g., X-axis) as the scanning line beam is scanned in another dimension (e.g., Y-dimension), such as illustrated in FIG. 4.

FIG. 6 illustrates a simplified, so-called "scan-non-descan" scanning configuration wherein a scanning line beam 115 illuminates scan lines L1 to Li (e.g., narrow line or broad line) traversing a sample 109 in one dimension (e.g., X-axis) as the scanning line beam 115 is scanned in another dimension (e.g., Y-dimension), such as illustrated in FIG. 4. All elements in FIG. 6 similar to those of FIGS. 3 to 5 have similar reference characters and are defined above. The returning (e.g., reflected or scattered) light 116 is permitted to likewise scan across a photodetector 107 (e.g., full-frame digital camera), which may optionally be coupled to a CPU for further processing and to a monitor for displaying a full-frame image, as illustrated in FIG. 5. In the present example of FIG. 6, photodetector 107 may be a full-frame digital camera and the returning light 116 may "paint" a full-frame image as it scans across a 2D photosensor array (e.g., active pixel array 134 of FIG. 5) of the camera. That is, each detected line of returning light 16 may be captured, buffered, and processed to construct a composite full-frame image, either with a single acquisition for the full-frame image, or through multiple acquisitions that make up the full frame. A radiation source 101 (e.g. light source, such as a laser, lamp, or LED) produces an illumination line beam 103 (non-coherent light beam or laser beam). A radiation aperture 105, imaged to the sample 109 (e.g., surface that is to be imaged), may be placed in front of radiation source 101 to help shape the illumination line beam 103. In the case of a fundus scan imager, radiation aperture 105 may be imaged to the retina of an eye. Illumination line beam 103 may pass through one or more optics (e.g., a lens) 111 before reaching a scanning component (e.g., galvo mirror) 113, which creates a scanning line beam of radiation (e.g., scanning line beam 115) that defines illumination lines L1 to Li across sample 109. In the present example, scanning line beam 115 output from scanning component 113 may pass through a scan lens 117 and ophthalmic lens 119, as described above, before reaching the sample 109 (e.g., a retina, or fundus, of an eye). In the present example, scanning line beam 115 output from scanning component 113 is scanned vertically (e.g., Vscan as illustrated in FIG. 4) in steps along the sample 109. Scattered light 116 returning from the sample 109 may pass through an aperture 123 in scanning component 113 (or otherwise conveyed from sample 109) to photodetector 107, and may likewise scan vertically in corresponding steps on the 2D photosensor array of photodetector 107. A more practical application may include a lens system 121, which may include second scan lens 121a and focusing lens 121b in front of the photodetector 107. In the case of a fundus scan imager, scanning component 113 may be substantially optically conjugate to the pupil of the eye.

As is explained above, an ROI speeds up an image capture sequence of a camera to the point where each scanning position (or step) of the image scanner may be imaged individually. Additionally, an ROI may effectively create a digital shutter since only pixels within the ROI are captured and read. This can lead to improved imaging. However, the present scanning configuration requires that the returning light be scanned across the 2D photosensor array of detector 107, which complicates, if not precludes, the use of ROIs. This is because it has heretofore not been possible to define new ROIs in between scanning positions of a scanning sequence. Although cameras that support multiple ROIs within a single image capture sequence of a camera are known, they are limited to a small number of ROIs so that one cannot define enough ROIs, nor control their image-capture sequence to follow the scanning operation of a scan imager.

As it is explained above, a full-frame camera may use a rolling shutter or global shutter technique to capture an entire full-frame a single image capture sequence (e.g. operation). It is often preferred to use a global shutter, full-frame camera in fundus imagers in order to avoid image artifacts caused by the rolling shutter effect, as is explained above. However, U.S. Pub. 2010/0128221, herein incorporated in its entirety by reference, describes the use of a rolling shutter CMOS camera in a line scan imager. In this case, a very narrow illumination light beam is used to scan across the retina, such that each illumination line beam corresponds to one pixel row of the camera's rolling shutter, 2D sensor array. Each returning line of light from the retina is carefully timed and mapped to each sequentially captured pixel row of the 2D sensor array as the 2D sensor array implements its rolling shutter sequence within a single full-frame, image-capture operation (e.g., a single shutter operation) of the camera. As it would be understood, however, this operation does not define any ROIs in the camera.

Some of the benefits of the scan-non-descan system of FIG. 6, such as simplified image capture architecture, and the scan-descan system of FIGS. 3 and 5, such as the steady (non-scanned) returning light that facilitate the use of an ROI or line scan camera, may achieved in a third scanning configuration, which is herein termed "scan-descan-rescan".

Figure 7:
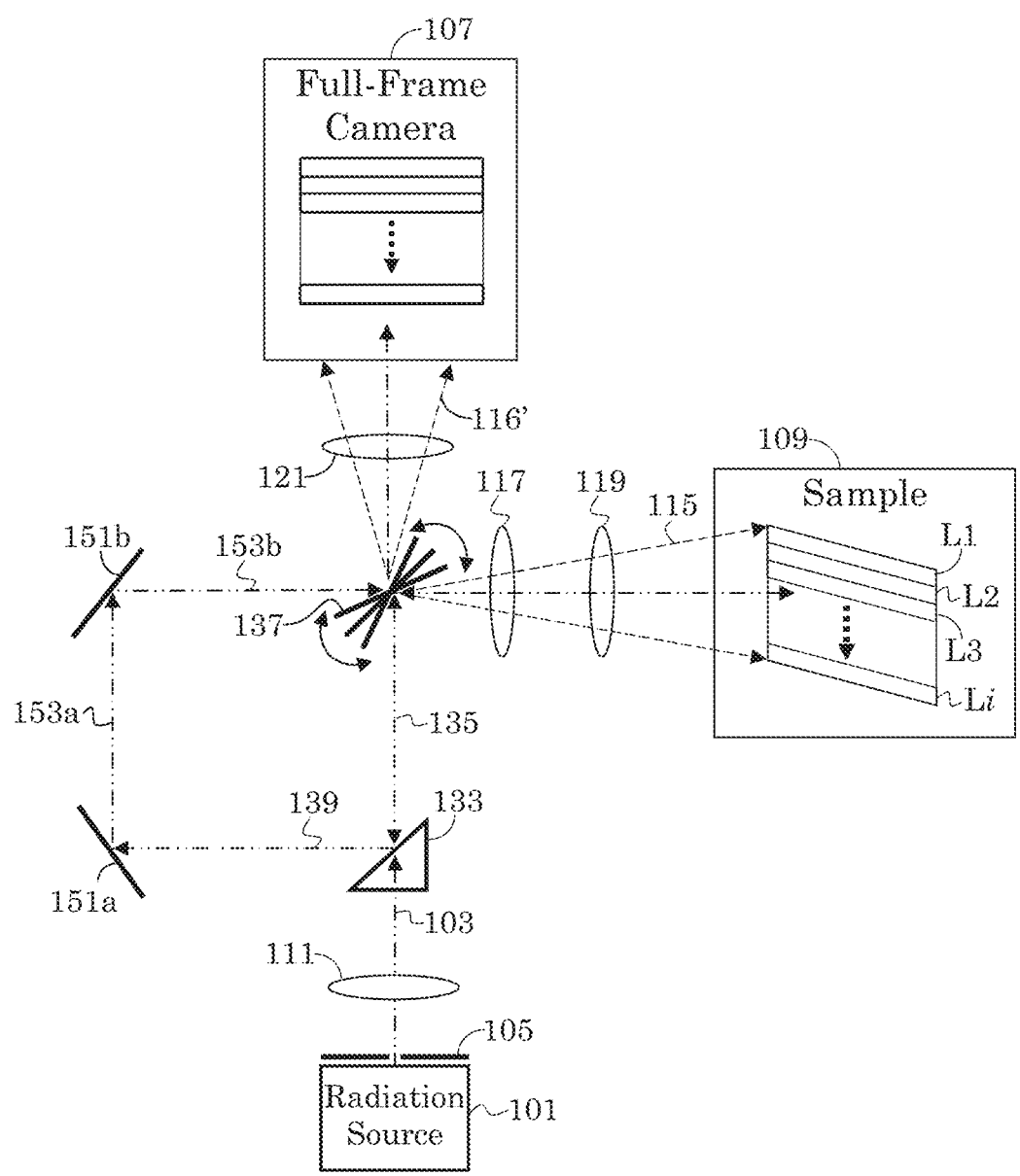
FIG. 7 illustrates a simplified scan-descan-rescan system, wherein a secondary scanning mechanism may be incorporated into a scan-descan system so as to scan anew (e.g., rescan) the otherwise non-scanning (e.g. descanned), returning, scattered light produced by the scan-descan system before it reaches the detector.

FIG. 7 illustrates a simplified scan-descan-rescan system, wherein a secondary scanning mechanism may be incorporated into a scan-descan system so as to scan anew (e.g., rescan) the otherwise non-scanning (e.g. descanned), returning, scattered light produced by the scan-descan system before it reaches the detector. All elements in FIG. 7 similar to those of FIGS. 3, 5, and 6 have similar reference characters and are described above. As before, a radiation source 101, with optional aperture 105 and collimating lens 111, creates an illumination line beam 103 that passes through beam splitter 133 onto optical path 135 to reach scanning component (e.g., galvo) 137. Scanning component 137 converts the received illumination beam into a scan beam (e.g. scanning line beam 115) that may pass through a scan lens 117 and an ophthalmic lens 119 to scan across a sample 109 (e.g., retina, or fundus, of an eye). As in the case of FIGS. 3 and 5, light returning from sample 109 is descanned by scanning component 137 to create a substantially steady, returning line beam on optical path 135, which is directed by beam splitter 133 onto collection path 139. At this point, the descanned, returning light on collection path 139 may be directed, such as by use of one or more mirrors 151a/151b along optical paths 153a and 153b to a second scanning mechanism. In the present example, the back of the galvo (scanning component 137) is reflective and used as the second scanning mechanism in order re-scan the returning light, and define a re-scanned returning light beam 116' on detector 107, via focusing lens 121. Since the scan beam 115 and re-scanned returning light beam 116' are defined together by scanning component 137, they correspond to each other.

Additional examples of scanning configurations used in fundus scan imagers are provided in U.S. Pat. No. 9,549,672, assigned to the same assignee as the present application and herein incorporated in its entirety by reference.

As is explained above, the illumination line that is scanned across the sample may be of different widths, but the width is typically fixed during any given scanning sequence. However, it may be beneficial to vary the width of the illumination line within the same scanning sequence. For example, it may be beneficial to increase the width of the illumination line at regions farther from the center of the fundus, but this may pose some difficulty in some scan configurations, particularly if one wishes to use ROIs.

Figure 8C:
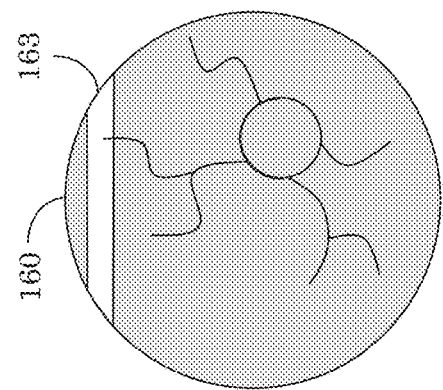
FIGS. 8A, 8B and 8C each illustrate differently sized illumination lines for scanning across a fundus area.
Figure 8B:
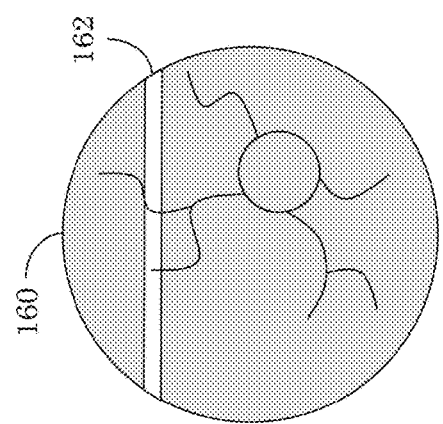
Figure 8A:
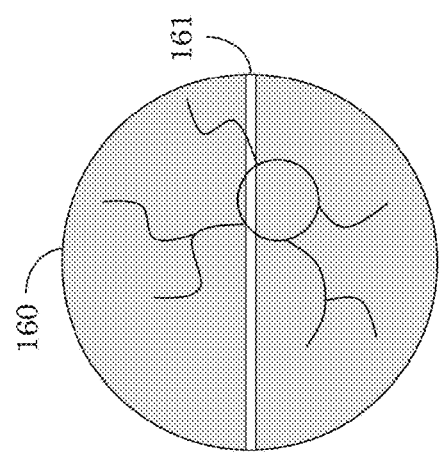

FIGS. 8A, 8B and 8C each illustrate differently sized illumination lines 161, 162 and 163 for scanning across a fundus area 160. In each of FIGS. 8A, 8B and 8C, illumination lines 161, 162, and 163 are illustratively shown as being of different widths. Each illumination line 161, 162, and 163 corresponds to the location of a scan beam on the fundus at a particular scanning step or time. Note that the scan beam can be scanned either smoothly across the retina, or moved in steps. Increasing the width of an illumination line, such as illumination line 163 as compared to illumination line 161, increases the amount of light applied and may provide an improved dynamic range, and/or help compensate for beam distortion at extreme scan angles.

Optionally, the size of each vertical scan step (e.g., the change in each incremental scan position) of the scanning mechanism (e.g., 113/137) may be made smaller than the width of an illumination slit, such that multiple consecutive illumination lines may overlap and cover the same region of a retina. In this manner, multiple image captures of returning light lines (e.g., image strips) will image the same region of the retina. This permits the use of various image processing techniques to improve the image quality of an individual imaged region. For example, image information from different image strips that correspond to the same retina region may be averaged. Alternatively, one may select an imaged portion of superior image quality (e.g., artifact-free portions) from among multiple overlapping image strips that may define an improved, composite image strip that may, in turn, be used in the construction of a composite, full-frame fundus image. For example, if a particular retina region is prone to errors, such as due to reflex, then non-error portions from different and corresponding captured scan lines can be pieced together to reconstruct an image of the error-prone region without errors. It is to be understood that all the illumination lines may optionally have the same width as they are scanned across the retina (e.g., the subject being imaged) without deviating from the present invention. Nonetheless, in embodiments, the width of the illumination lines may be changed as one scans across the retina, such as to provide greater illumination at regions closer to extreme edges of the retina. For example, illumination line 161 near the center of the retina may be thinner than illuminations line 162, which in turn may be thinner than illumination 163 near the top edge of the retina. This change in width may be continuous and smooth, or may be in discrete steps, such as if the area to be scanned is divided into sectors and the scan lines applied to each sector have a different, fixed width.

This enhancement, however would be difficult, if not impossible, to implement in a scan-non-descan system since the overlapping regions would overwrite each other on the 2D sensor array. Use of ROIs may avoid the overwriting issue, but current cameras cannot update ROIs quickly enough to separately capture each overlapping scan line position at a typical fundus scanning rate. One may consider using a full-frame camera in a scan-descan configuration with a single ROI that does not change during the scanning operation and receives a steady, non-scanning returning light line irrespective of the scan position. However, this approach would require that the ROI be sufficiently large enough to capture the widest illumination scan line, which means that the ROI would capture excess scatter light (from outside an illumination scan line) when capturing returning light from thinner illumination scan lines. This may effectively defeat some of the light filtering benefits of an ROI and may provide less than optimal imaged strips when imaging returning light from thinner illumination lines.

Currently, once a particular scanning configuration and its associated line scanning beam pattern and camera are selected, it can be very difficult to introduce alterations to those selections. Furthermore, it has heretofore not been possible to introduce variability into ROIs within a single scanning sequence. For example, once a particular width for an illumination light is selected, and its corresponding ROI is defined within a digital camera before the start of a scanning sequence, it has not been possible to introduce adjustments to the ROI to compensate for changes in the illumination line during the same scanning sequence while maintaining typical fundus scanning rates. This may be a limitation of the camera, or at least of its command and control interface, since it has not previously been possible to alter an ROI quickly enough between image capture sequences of the camera. Thus, implementing a scan imager with a varying width illumination line using a 2D sensor array and correspondingly adjusted ROIs has not been feasible.

Below is presented a camera architecture with improved ROI control suitable for use in a scan imager. The present implementation overcomes some of the limitations of current ROI-capable cameras, and particularly improves the speed of ROI update implementation to permit on-the-fly ROI changes within a single scanning operation of a scan imager.

As is explained above, certain optical artifact issues could be resolved by capturing a series of image strips (e.g., captured returning light lines) and montaging together artifact-free portions of the image strips. A full-frame image, which includes many image strips, should be captured in less than 0.12 seconds in order to avoid the start of pupil reflex, which may introduce motion artifacts, obscure part of the image, and/or darken the image. A large number of overlapping image strips (e.g., 100 to 200 image strips) should be captured within this 0.12 second time limit to construct a full-frame image. The present invention may advantageously use a different ROI (e.g., of indefinite width, length, and/or position) for each image strip. To achieve this, a Y-Offset of an ROI (and optionally its width, length, and/or X-Offset position definition) may be changed or changed/shifted after each image strip is captured and, before an immediately following scanning line position is be captured, to meet a given scanning time restriction (e.g., the 0.12 second scanning sequence time limit). This may include writing a new Y-Offset value to a register (e.g., an ROI-definition record) in the image sensor. Preferably, this write operation would be synchronized with the exposure and readout timing of the sensor. Doing this over a typical camera's communication interface (USB3® or Camera-Link®) would be too slow to meet the 0.12 second time restriction.

The present invention therefore provides an enhanced camera architecture, which may include a specialized controller and/or circuitry that sets camera capture parameters, including ROI size (optionally including shape) and location, and that permits updating an ROI Y-Offset register (and optionally other registers, as needed) during the Frame-Overhead-Time (FOT) of the camera. The FOT may generally be defined as the time between the end of sensor integration (e.g., pixel exposure time) and the start of sensor readout, and it is typically a wait period within the camera's operations. The present invention takes advantage of the FOT wait period by updating an ROI (e.g., updating the ROI-definition record) during the FOT wait period in preparation for the next exposure.

The controller may control the exposure duration of the sensor, such as by use of a Start-Exposure signal and Stop-Exposure signal. For example, an executable program (e.g., executed within a processing unit, controller, or state machine) on the camera may set the exposure time, and issue the Start-Exposure signal (e.g. send a signal pulse to the sensor) to start exposure of an ROI, and the camera controller may issue the Stop-Exposure signal (e.g., pulse on a Stop-Exposure signal line) when the previously set exposure time elapses/ends. This process may be implemented as a state machine in a programmable logic device, such as a field programmable gate array, FPGA, within the camera and thereby always know where in the exposure process it is. These operations would be executed within a camera in accord with the present invention. In prior art cameras, when it was desired to alter an ROI, instructions for altering the ROI would need to be input to the camera via a communication interface, such as via an USB® interface. This typically required the use of a specialized software interface, such as an application programming interface, API. To avoid scrambling an image, such prior art applications would need to wait until the data from a previous exposure had been read out before inputting the ROI update. This would lead to too much latency and prevent the capture of high-resolution scan images in the required 0.12 second limit of a scan imager.

Figure 9:
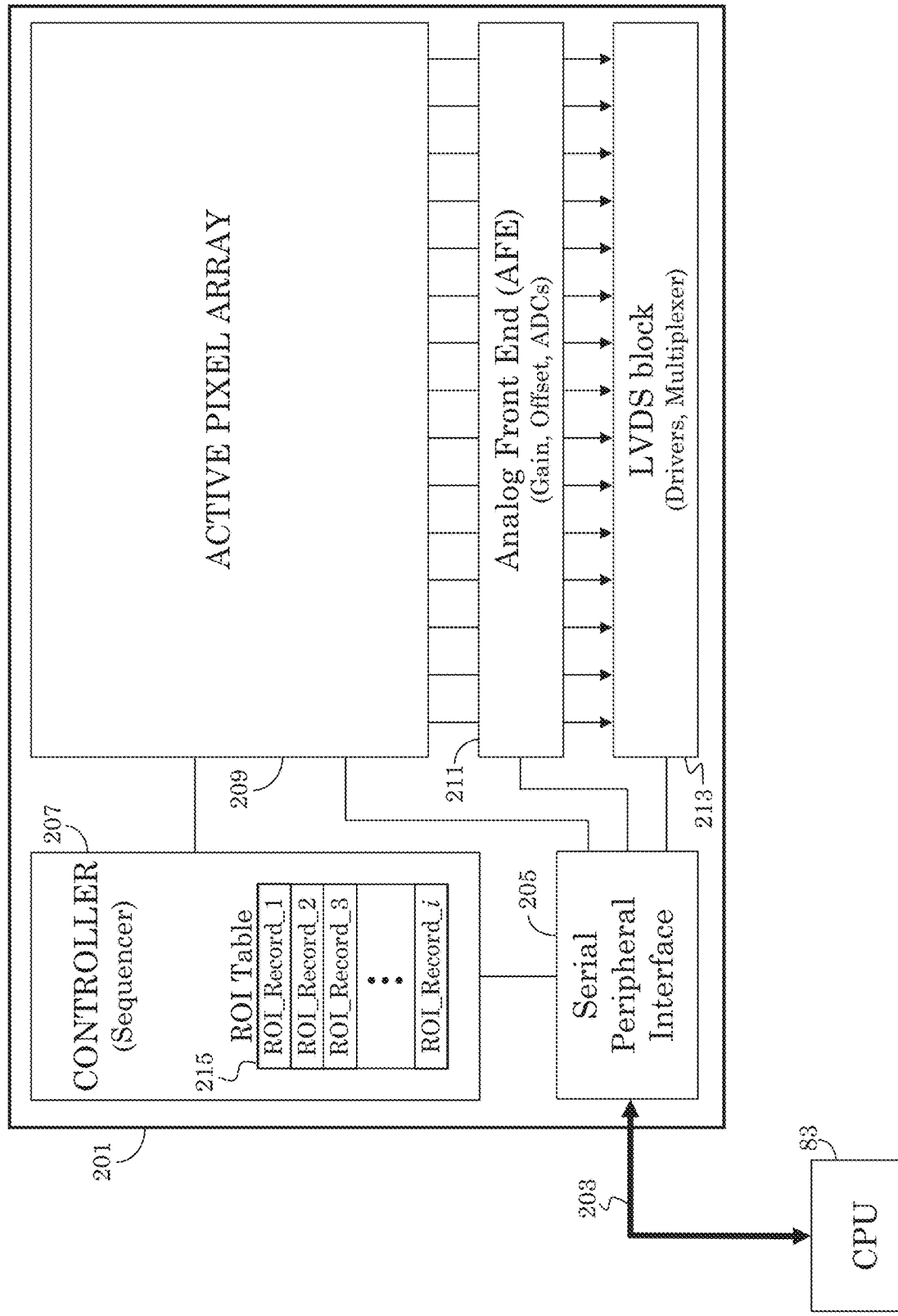
FIG. 9 illustrate an exemplary internal structure of a camera in accord with the present invention.

FIG. 9 illustrates an exemplary internal structure of a camera 201 in accord with the present invention. As shown, a CPU (or computing device or computer system) 83 may communicate with camera 201 by means of a communication link 203, such as a USB® or CameraLink® serial communication link. Internally, communication to/from CPU 83 may be handled by a Serial Peripheral Interface (SPI) block 205, or other appropriate communication interface. SPI is a synchronous serial communication interface specification commonly used in industry for short distance communication, primarily in embedded systems, and may be used in some digital cameras. Internally, SPI block 205 may relay communications between multiple internal component blocks. For example, SPI block 205 may relay instructions received from CPU 83 to a controller (or sequencer) 207, whose function may be to control the operation of an active pixel array (e.g., sensor) 209. That is, sequencer 207 may generate the necessary signals for image acquisition. The image is captured by active pixel array (or sensor) 209, which may be a global shutter array or a rolling shutter array. Sensor 209 preferably supports one or more ROIs, as defined by use of one or more ROI-definition records (e.g., registers). Internally, sensor 209 may consist of a 2D array of photosensitive elements (e.g., pixels), and integrates photonic energy received at a region of interest within the 2D array, as defined by a specific ROI entry. After a period of sensor integration (e.g., exposure time) during which the photosensitive elements are exposed to incoming light and permitted to reach a final state of sensed photonic energy (e.g., signal information), the current state of the pixels within a selected ROI may be captured by being transferred to an analog front end (AFE) block 211, where the captured signal data from each pixel may be amplified (e.g., by use of a column amplifier block) and converted to digital form (e.g., by use of a column analog-to-digital converter (ADC) block). This may effectively define an image strip that may then be read out (e.g. sequentially, row-by-row). As it would be understood, it takes time for the pixel information to be transferred, captured, and conditioned by AFE block 211 in preparation for the image data to be read out. This time may be part of a time delay between the end of sensor integration (e.g., pixel exposure time) and the start of sensor readout, which may be part of the Frame-Overhead-Time, FOT. The captured pixel information may then be read out by using appropriate output drivers using a suitable communication protocol. In the present example, the camera uses low voltage differential signaling, LVDS, (a high speed, serial communication protocol). Thus, during a read phase, image data from AFE block 211 is passed to an LVDS block 213, which may output the captured pixel information to an external component, such as CPU 203.

In the present embodiment, controller (or sequencer) 207 may hold one or more ROI tables 215. The controller 207 may include, or be in communication with, a programmable logic device that implements a state machine that modifies ROIs within sensor 209 during a scanning operation/sequence of a scan imager in accordance with a currently selected ROI Table. Optionally, each of the one or more ROI tables may define a different scanning modality. A scan imager may support multiple different imaging modalities, such as infrared or visible imaging, color imaging, and/or florescence imaging. Each imaging modality may have different imaging requirements, such as different exposure times and/or multiple pulse integration of light signal for higher dynamic range. For example, an image capture sequence may include illumination by a plurality of light wavelength bandwidths applied in sequence, and repeated image-capture-and-read-out operations. The requirements of each imaging modality may be included in each respective ROI Table.

FIG. 10 illustrates an exemplary ROI Table 215, which may be comprised of multiple rows of information (e.g., multiple entries). Each row may define a different region of interest for a given imaging modality, and may include additional image capture (or exposure) parameters. For example, exposure times may need to be changed for individual scan lines that are to be imaged.

ROI Table 215 may be a block of memory that contains a series of parameter sets. Each parameter set may be arranged in 'rows' that define each ROI (or strip) that corresponds to each scan line to be captured, wherein 'columns' of data corresponding to each parameter to be changed between image capture operations of sequential scan lines. ROI Table 215 may be implemented as RAM in an FPGA, as low-latency memory in a real-time processor, or in other types of storage such as a bank of active registers or long term storage. A state machine (which may be part of sequencer 207 as discussed above) may read a current ROI table entry (e.g., a current row, or record, within ROI Table 215), and transmit that entry's parameters to sensor 209 (e.g., to the sensor's ROI-definition record), and advance a table pointer (e.g., ROI_Pointer_1) to the next entry. The transferred parameters may be written to one or more registers that define the ROI-definition record used to define/construct a region-of-interest within sensor 209. ROI Table 215 may have one row per scan line in a one-to-one arrangement. For example, if a scan imager defines scan lines L1 to Li during a scanning sequence, such as discuss above, then ROI Table 215 may have i corresponding row entries, ROI_1 to ROI_i.

ROI Table 215 may have multiple columns, each defining a different parameter of an ROI setting (and optionally additional imaging settings). For example, a first column 221 may identify a specific ROI by ID number. A second column may define a Y-Offset that indicates the y-position (e.g., pixel row number) that corresponds to the top of a current ROI. This Y-Offset may be referenced to the topmost row of the sensor array 209 (e.g., Pixel_Row_0, not shown), or may be a Y-Offset from the most previously ROI position. Each ROI may define multiple rows, and so column 223 indicates the number of pixel rows in the current ROI (e.g., Y-size, or width). For example, the number of rows may correspond to the width of a given scan line on a sample. Optionally, an ROI may define a fraction of a row, in which case an X-Offset entry and x-length entry may also be included, as indicated by columns 224 and 225, respectively. Different lighting conditions may require different exposure times, and so ROI Table 215 may also include columns to define imaging instructions, such an exposure time in column 226, which indicates how long the ROI should be exposed (e.g., integration time) before being captured (e.g., transferred to AFE block 211) in preparation for being read out.

In operation, the Sequencer 207 may use a table pointer (or other tracking system) to identify one or more current rows/entries within the ROI table that are being used to define one or more current regions of interest within sensor 209. For example, if the scan imager defines a single line of illumination that is scanned across a sample to be imaged, then sequencer 207 may point to (and extract information from) the corresponding, single row in ROI Table 215. Alternatively, if the image scanner defines two or more illumination lines (e.g., scan lines) and scans these illuminations lines concurrently across a sample, then Sequencer 207 may use two or more table pointers (e.g., ROI_Pointer_1 and ROI_Pointer_2) to identify and access two or more rows within ROI Table 207 that correspond to the two or more current scan lines. This may be the case, for example, if the scan imager uses a first horizontal scan line to scan from the top of a sample toward the bottom (or midpoint) of the sample, while concurrently using a second horizontal scan line to scan from bottom of the sample toward the top (or midpoint) of the sample.

To achieve the present operation, sequencer 207 inserts new ROI-updating states into a phase of a typical image capture process/sequence. In the present embodiment, these new ROI-updating states (wherein information from ROI Table 215 are used to update image capture settings, e.g. specific registers, that control the operation of sensor 209) may be updated during the sensor's Frame Overhead Time, FOT, but they may also be updated within any phase of the image capture process where the update may be safely executed, e.g., wherein the update will not disrupt the normal image capture process. Sequencer 207 may keep track of which ROI (e.g. strip region within the sensor) is to be exposed, and updates an index to ROI Table 215 during each exposure. It is not important exactly when the index is updated, as long as the new values (parameter settings from ROI Table 215) are ready to be transferred to the sensor before FOT is reached.

ROI Table 215 may be loaded into camera 201 before the start of a scanning operation. For example in the case of a fundus scan imager being used for an eye exam, at the beginning of an exam, ROI Table 215 may be loaded with parameter values to be used for the scanning operation of the fundus scan imager. These values may be provided by a host application (e.g., running on CPU 83) via the camera's command and control interface. This interface may be an USB3® data interface, but may be any type communication interface, such as RS-232, USB1®, USB2®, Ethernet, Wi-Fi™, etc.

Figure 11:
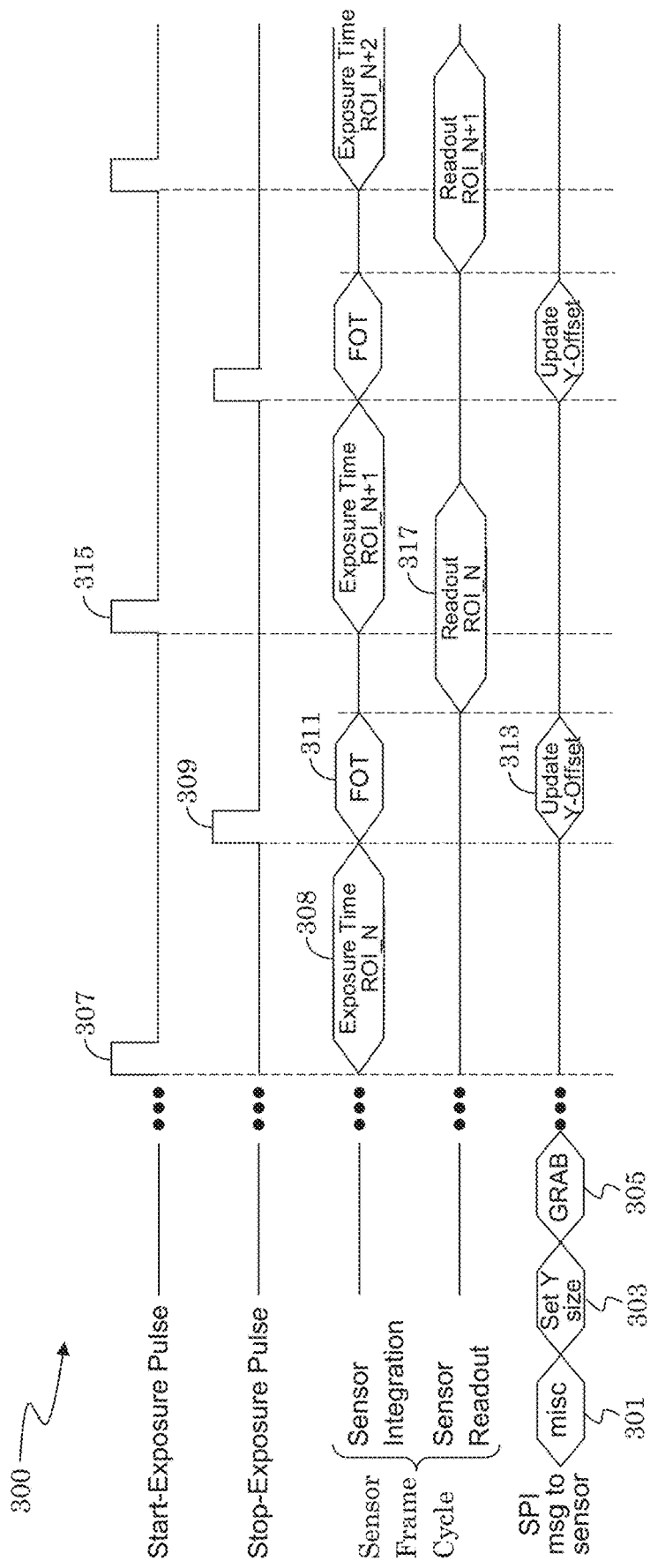
FIG. 11 provides a timing diagram showing the updating of ROI setting within a sensor array in accord with the present invention.

FIG. 11 provides a timing diagram 300 showing the updating of ROI settings within a sensor array in accord with the present invention. In essence, all ROI updates from ROI Table 215 are loaded to the sensor 209 during the sensor's FOT phase of operation. Preferably, before the start of a scanning operation, the sensor is first initiated (e.g., in response to a predefined cue) by transferring the first corresponding parameters from ROI Table 215 to the sensor. This may be in the form of SPI messages to the sensor. Various cues may be monitored to identify the impending start of a scanning operation. For example, a cue may be if an eye-alignment operation of the Fundus imager is executed, or if a specific one of multiple different ROI Tables is selected/loaded, or if a start-capture command is received, etc.

For ease of explanation, the present timing diagram example assumes multiple ROIs of fixed size (e.g., fixed number of rows, or Y size, and fixed length that includes an entire row size). This may be viewed as a fixed-size ROI that is shifted in the y-direction to follow a Vscan of the scanning beam, where the fixed-size ROI is shifted between the image-capturing of sequential scan lines. That is, a current ROI position is shifted by a specified Y-Offset amount before the capture of a next scan line. In this example, the initializing of the sensor may take the form of (following any miscellaneous communications 301), setting the Y-size 303 of the fixed-size ROI (e.g., from an ROI Table), and executing a GRAB (e.g., data transfer) operation 305 to sensor 209 (e.g., writing the y-size to a register of sensor 209). This GRAB may also include transferring the starting y-position of the fixed-size ROI if the starting position is not the zero position (e.g., top of the sensor array) by default. In operation, after receiving a start-capture command (or other cue indicating the start of a scanning operation), a Frame Trigger pulse may initiate the following sequence of events: (a) a 'start exposure' signal (or capture-start signal) 307 is pulsed, which starts an exposure time 308 that cause sensor 209 to capture an image (e.g., ROI image or strip) under the control of its internal registers, some of which have been written with values from the ROI Table 215. Following a prescribed exposure time, a 'stop exposure' signal (or capture-stop signal) 309 is pulsed, which starts the sensor's Frame Overhead Time, FOT, phase 311. During this FOT phase, the sensor may start the process of transferring pixel data from the captured region-of-interest set by the current ROI table entry to its AFE block. Between the time when the previous ROI parameters of ROI Table 215 were transferred to sensor 209 and the start of the current FOT 311, the ROI Table index (e.g., ROI_Pointer_1) is updated to point to the next ROI parameters in ROI Table 215 to be used with the next scan line image capture sequence. Data from the newly-indexed ROI Table entry is transferred to sensor registers during the current FOT 311. In the present example, this may include updating the Y-Offset 313 information in sensor 209 so as to y-shift the fixed-size ROI by a desired amount prior to initiating the next image capture sequence of the next scan line, as indicated by the next start-exposure pulse 315. Following the FOT 311, pixel data is transferred out of the sensor 209 by a read operation 317, at which time the sensor may be ready for the next 'start exposure' pulse. This process may repeat to the end of the ROI Table 215. Optionally, a scanning operation may stop when the end of the ROI Table is reached. Alternatively, some scanning operations may set the table index back to the first entry of the ROI Table, load the sensor's registers with that entry's data, and wait for another frame-triggering event.

Figure 12:
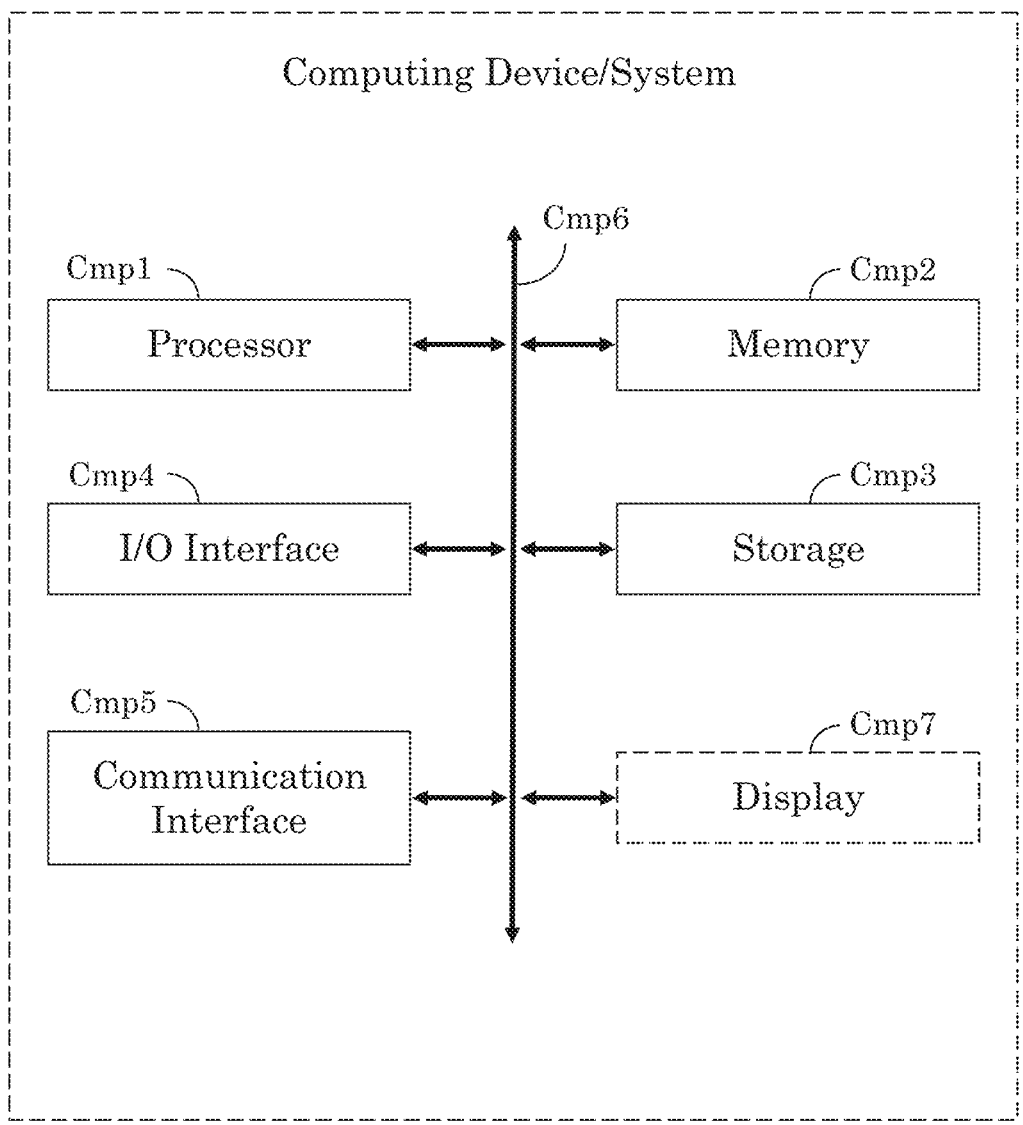
FIG. 12 illustrates an example computer system (or computing device or computer device).

FIG. 12 illustrates an example computer system (or computing device or computer device). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cmp1, memory Cmp2, storage Cmp3, an input/output (I/O) interface Cmp4, a communication interface Cmp5, and a bus Cmp6. The computer system may optionally also include a display Cmp7, such as a computer monitor or screen.

Processor Cmp1 includes hardware for executing instructions, such as those making up a computer program. For example, processor Cmp1 may be a central processing unit (CPU) or a general-purpose computing on graphics processing unit (GPGPU). Processor Cmp1 may retrieve (or fetch) the instructions from an internal register, an internal cache, memory Cmp2, or storage Cmp3, decode and execute the instructions, and write one or more results to an internal register, an internal cache, memory Cmp2, or storage Cmp3. In particular embodiments, processor Cmp1 may include one or more internal caches for data, instructions, or addresses. Processor Cmp1 may include one or more instruction caches, one or more data caches, such as to hold data tables. Instructions in the instruction caches may be copies of instructions in memory Cmp2 or storage Cmp3, and the instruction caches may speed up retrieval of those instructions by processor Cmp1. Processor Cmp1 may include any suitable number internal registers, and may include one or more arithmetic logic units (ALUs). Processor Cmp1 may be a multi-core processor; or include one or more processors Cmp1. Although this disclosure describes and illustrates a particular processor, this disclosure contemplates any suitable processor.

Memory Cmp2 may include main memory for storing instructions for processor Cmp1 to execute or to hold interim data during processing. For example, the computer system may load instructions or data (e.g., data tables) from storage Cmp3 or from another source (such as another computer system) to memory Cmp2. Processor Cmp1 may load the instructions and data from memory Cmp2 to one or more internal register or internal cache. To execute the instructions, processor Cmp1 may retrieve and decode the instructions from the internal register or internal cache. During or after execution of the instructions, processor Cmp1 may write one or more results (which may be intermediate or final results) to the internal register, internal cache, memory Cmp2 or storage Cmp3. Bus Cmp6 may include one or more memory buses (which may each include an address bus and a data bus) and may couple processor Cmp1 to memory Cmp2 and/or storage Cmp3. Optionally, one or more memory management unit (MMU) facilitate data transfers between processor Cmp1 and memory Cmp2. Memory Cmp2 (which may be fast, volatile memory) may include random access memory (RAM), such as dynamic RAM (DRAM) or static RAM (SRAM). Storage Cmp3 may include long-term or mass storage for data or instructions. Storage Cmp3 may be internal or external to computer system, and include one or more of a disk drive (e.g., hard disk drive, HDD, or solid state drive, SSD), flash memory, ROM, EPROM, optical disc, a magneto-optical disc, magnetic tape, Universal Serial Bus (USB)-accessible drive, or other type of non-volatile memory.

I/O interface Cmp4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device or a combination of two or more of these.

Communication interface Cmp5 may provide network interfaces for communication with other systems or networks. Communication interface Cmp5 may include a Bluetooth interface or other type of packet-based communication. For example, communication interface Cmp5 may include a network interface controller (NIC) and/or a wireless NIC or a wireless adapter for communicating with a wireless network. Communication interface Cmp5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cmp6 may provide a communication link between the above mentioned components of the computing system. For example, bus Cmp6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

We claim:

1. A camera comprising:
   an image sensor array;
   a region-of-interest (ROI) definition record that defines a region of interest within the image sensor array; and
   control circuitry implementing the following operations:
   (i) an image capture sequence, including:
      initiating exposure of the sensor array to image the defined region of interest in response to a capture-start signal;
      terminating the exposure of the sensor array in response to a capture-stop signal;
      reading out image data of the defined region of interest;
   (ii) updating the ROI-definition record during the execution of the image capture sequence; and
   (iii) repeating steps (i) and (ii) a plurality of times, each time imaging a defined region of interest based on the ROI-definition record updated during the previous image capture sequence.

2. The camera of claim 1, wherein the ROI-definition record is updated after terminating the exposure of the sensor array and before reading out image data of the defined region of interest.

3. The camera of claim 1, further comprising:
   a table of ROI entries, each ROI entry defining a different region of interest;
   a pointer pointing to a first ROI entry within the table of ROI entries;
   wherein the updating of the ROI-definition record includes updating the pointer to point to a second ROI entry within the table or ROI entries.

4. The camera of claim 3, wherein:
   the camera supports a plurality of different image capture modalities, each having a corresponding different table of ROI entries.

5. The camera of claim 1, wherein:
   the camera is configured to image individual, consecutive scan lines from a scan imager during a scanning sequence of the scan imager; and
   the ROI-definition record is updated in between the imaging of consecutive scan lines within the scanning sequence.

6. The camera of claim 1, wherein the updating of the ROI-definition record offsets a position of the defined ROI within the sensor array in at least one of an X-axis direction or Y-axis direction.

7. The camera of claim 1, wherein the ROI-definition record includes at least one register, and updating the ROI-definition record includes updating the at least one register with new ROI data.

8. The camera of claim 1, wherein the camera is a fundus imaging camera; and
   each ROI defines a fraction of the sensor array;
   each updated ROI-definition record defines a new fraction of the sensor array that partially overlaps a previous fraction of the sensor array defined by a previous ROI.

9. The camera of claim 1, wherein updating the ROI-definition record is controlled by a state machine within the camera.

10. The camera of claim 1, wherein updating the ROI-definition record changes the size of the region of interest within the image sensor array.

11. The camera of claim 10, wherein updating the ROI-definition record changes the location of the region of interest within the image sensor array.

12. A method for controlling a camera, comprising:
    defining a region-of-interest (ROI) in a sensor array of the camera in accordance with an ROI-definition record;
    (i) executing an image capture sequence, including:
       initiating exposure of the sensor array to image the defined ROI in response to a capture-start signal;
       terminating the exposure of the sensor array in response to a capture-stop signal;
       reading out the captured image data of the ROI;
    (ii) updating the ROI-definition record during the execution of the image capture sequence, and
    (iii) repeating steps (i) and (ii) a plurality of times, each time imaging a defined ROI based on the ROI-definition record updated during the previous image capture sequence.

13. The method of claim 12, wherein the ROI-definition record is updated following the terminating of the exposure of the sensor array.

14. The method of claim 13, wherein the ROI-definition record is updated before the start of the reading out of the captured image data.

15. The method of claim 12, wherein the updating of the ROI-definition record offsets a position of the defined ROI within the sensor array in at least one of an X-axis direction or Y-axis direction.

16. The method of claim 12, wherein the ROI-definition record includes at least one register, and updating the ROI-definition record includes updating the at least one register with new ROI data.

17. The method of claim 12, wherein:
    multiple regions-of-interest are defined within an ROI Table;
    the camera includes a pointer pointing to a first row within the ROI table; and
    updating the ROI-definition record includes updating the pointer to point to a second row within the ROI Table.

18. The method of claim 12, wherein:
    the ROI-defining record is updated in accordance with an ROI Table of entries, each entry defining a different ROI; and
    the camera supports a plurality of different image capture modalities, each image capture modality having a corresponding different ROI Table.

19. The method of claim 12, wherein:
    the camera is configured to image individual, consecutive scan lines from a scan imager during a scanning sequence of the scan imager; and
    the ROI-definition record is updated in between the imaging of consecutive scan lines within the scanning sequence.

20. The method of claim 12, wherein:
    the camera is a fundus imaging camera;
    each ROI defines a fraction of the sensor array;
    each updated ROI-definition record defines a new fraction of the sensor array that partially overlaps a previous fraction of the sensor array defined by a previous ROI.

21. The method of claim 12, wherein updating the ROI-definition record is controlled by a state machine within the camera.

\* \* \* \* \*